US009487575B2

(12) United States Patent
Farias-Eisner et al.

(10) Patent No.: US 9,487,575 B2
(45) Date of Patent: Nov. 8, 2016

(54) COMPOSITIONS AND METHODS FOR TREATMENT OF GYNECOLOGIC CANCERS

(75) Inventors: Robin Farias-Eisner, Calabass, CA (US); Srinivasa T. Reddy, Cerritos, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 386 days.

(21) Appl. No.: 13/877,649

(22) PCT Filed: Oct. 4, 2011

(86) PCT No.: PCT/US2011/054817
§ 371 (c)(1),
(2), (4) Date: Apr. 3, 2013

(87) PCT Pub. No.: WO2012/047930
PCT Pub. Date: Apr. 12, 2012

(65) Prior Publication Data
US 2013/0217636 A1 Aug. 22, 2013
US 2014/0088018 A9 Mar. 27, 2014

Related U.S. Application Data

(60) Provisional application No. 61/389,618, filed on Oct. 4, 2010.

(51) Int. Cl.
*C07K 14/775* (2006.01)
*A61K 38/17* (2006.01)

(52) U.S. Cl.
CPC ......... *C07K 14/775* (2013.01); *A61K 38/1709* (2013.01)

(58) Field of Classification Search
None
See application file for complete search history.

(56) References Cited

U.S. PATENT DOCUMENTS

| | | | |
|---|---|---|---|
| 5,114,863 A | 5/1992 | McCombs et al. | |
| 5,876,968 A * | 3/1999 | Sirtori et al. | 435/69.7 |
| 5,891,641 A | 4/1999 | Prusiner et al. | |
| 5,955,582 A | 9/1999 | Newman et al. | |
| 7,191,068 B2 | 3/2007 | Rosenfeld et al. | |
| 7,291,461 B2 | 11/2007 | Welch | |
| 7,427,662 B2 | 9/2008 | Hornick et al. | |
| 7,510,842 B2 | 3/2009 | Produst et al. | |
| 7,510,881 B2 | 3/2009 | Ramael et al. | |
| 7,575,876 B2 | 8/2009 | Zhang et al. | |
| 7,589,174 B2 | 9/2009 | Argon et al. | |
| 7,604,948 B2 | 10/2009 | Amaral et al. | |
| 7,605,003 B2 | 10/2009 | Chan et al. | |
| 7,670,792 B2 | 3/2010 | Farias-Eisner et al. | |
| 7,723,303 B2 | 5/2010 | Fogelman et al. | |
| 8,323,915 B2 | 12/2012 | Farias-Eisner et al. | |
| 2003/0027216 A1 | 2/2003 | Kiernan et al. | |
| 2005/0059013 A1 | 3/2005 | Chan et al. | |
| 2005/0172359 A1 * | 8/2005 | Moloney et al. | 800/281 |
| 2005/0214760 A1 | 9/2005 | Chan et al. | |
| 2006/0068405 A1 | 3/2006 | Diber et al. | |
| 2006/0094039 A1 | 5/2006 | Rosenfeld et al. | |
| 2006/0257866 A1 | 11/2006 | Welch et al. | |
| 2007/0031379 A1 | 2/2007 | Lee et al. | |
| 2009/0246769 A1 | 10/2009 | Sato et al. | |
| 2010/0081151 A1 | 4/2010 | Farias-Eisner et al. | |
| 2010/0173788 A1 | 7/2010 | Goncalves et al. | |
| 2010/0227825 A1 | 9/2010 | Fogelman et al. | |
| 2011/0027894 A1 | 2/2011 | Farias-Eisner et al. | |
| 2013/0090256 A1 | 4/2013 | Farias-Eisner et al. | |

FOREIGN PATENT DOCUMENTS

| | | |
|---|---|---|
| EP | 0 201 187 | 11/1986 |
| EP | 1 789 805 | 9/2010 |
| EP | 2 199 801 | 5/2013 |
| WO | WO91/08488 | 6/1991 |
| WO | WO2004/012588 | 2/2004 |
| WO | WO2004/013609 | 2/2004 |
| WO | WO2005/093413 | 10/2005 |
| WO | WO 2006/099126 | 9/2006 |
| WO | WO2007/068985 | 6/2007 |

OTHER PUBLICATIONS

Van Lenten et al. (Curr. Atheroscler. Rep. 11: 52-57, 2009).*
Zhang et al. (Am. J. Physiol. Cell Physiol., 291: C1089-C1098, 2006).*
Sutphen et al. (Epidemiol. Biomarkers Prev., 13: 1185-1191, 2004).*
Xu et al. (Biochem. J., 309: 933-940, 1995), and Li et al. (Mol. Cancer Ther., 8: 1692-1701, 2009).*
Joy et al. (Nature Reviews/Drug Discovery, 7: 143-155, 2008).*
Li et al. (Mol. Cancer Ther., 8: 1692-1701, 2009).*
Jaspard et al. (Biochemistry, 35: 1352-1357, 1996).*
Kozak, Katherine R., "Identification of biomarkers for ovarian cancer . . . prognosis", PNAS, Oct. 14, 2003, 100(21): 12343-12348.
Kozak, Katherine R., "Characterization of serum biomarkers for detection of early stage ovarian cancer", Proteomics, 2005, 5: 4589-4596.
Munstedt, Karsten, "Impact of hemoglobin levels before and during chemotherapy . . . cancer", Intl. Journal of Oncology, 2003, 23: 837-843.
Obermair, Andreas, "The relationship of pretreatment serum hemoglobin level . . . patients", 1998, American Cancer Society, XP008056584, pp. 726-731.
Rai, Alex J., "Proteomic approaches to tumor marker discovery", Dec. 2002, Arch Pathol Lab Med, 126: 1518-1526.

(Continued)

*Primary Examiner* — Brad Duffy
*Assistant Examiner* — Nelson B Moseley, II
(74) *Attorney, Agent, or Firm* — Karen S Canady; canady + lortz LLP

(57) ABSTRACT

Molecules and compositions that can be used in the treatment of gynecologic cancers are described. ApoA-1, in particular, is demonstrated to inhibit the proliferation of cancer cells reduce tumor size in a mouse model of ovarian cancer.

14 Claims, 5 Drawing Sheets

(56) References Cited

OTHER PUBLICATIONS

Tockman, M. et al., "Considerations in Bringing a Cancer Biomarker to Clinical Application", Cancer Research, 1992, 52: 2711s-2718s.
Tosner, J., "Serum prealbumin, transferrin and alpha-1-acid glycoprotein in patients with gynecological carcinomas", 1988, Neoplasma, Sciences, 35(4):403-412.
Van Belle, S.J.-P, "What is the value of hemoglobin as a prognostic and predictive factor in cancer?", 2004, EJC Supplements, XP008056585, 2(2):11-19.
Zhang, Zhen, "Protein identification and immunoassay evaluation of a panel of biomarkers . . . ovarian cancer", AACR Meeting Abstracts Online, 2004, 45: Abstract #1063.
USPTO Office Action mailed on Oct. 11, 2012 in U.S. Appl. No. 12/860,293, filed Aug. 20, 2010.
Extended European Search Report dated Sep. 5, 2011 cited in corresponding EP Application No. 10009544.7, 10 pp.
Extended European Search Report dated Jul. 28, 2010, EP App. No. 10003541.9-1223.
Duk, J.M. et al., "CA 125: A useful marker in endometrial carcinoma", 1986, Amer J. of Obstetrics and Gynecology, 155(5): 1097-1102. 1 page Abstract.
Su, Feng et al., "Validation of candidate serum ovarian cancer biomarkers for early detection", Biomarker Insights, 2007, 2: 369-375.
Response as filed in EPO on Apr. 3, 2012, in corresponding EP App. No. 10009544.7-1223.
EPO Office Action dated Jul. 9, 2012, in corresponding EP Application No. 10009544.7-1223.
International Search Report + Written Opinion dated Apr. 27, 2012 in related PCT Application No. PCT/US2011/054817, filed Oct. 4, 2011.
Lo, S.S.T. et al., "Prognostic Significance of Tumour Markers in Endometrial Cancer", 1997, Tumor Biology, 18:241-249.

\* cited by examiner

COMPOSITIONS AND METHODS FOR TREATMENT OF GYNECOLOGIC CANCERS

This application claims the benefit of U.S. provisional patent application No. 61/389,618, filed Oct. 4, 2010, and is related to application Ser. No. 12/630,458, filed Dec. 3, 2009, which is a divisional of application Ser. No. 11/571,986, filed Jul. 18, 2007, now U.S. Pat. No. 7,670,792, which is a national stage filing under 35 U.S.C. 5371 of PCT/US2005/024985, filed Jul. 14, 2005, which claims the benefit of U.S. provisional patent application No. 60/674,489, filed Apr. 25, 2005, and 60/588,007, filed Jul. 14, 2004. In addition, this application is related to U.S. patent application Ser. No. 12/860,293, filed Aug. 20, 2010, which is also a continuation-in-part of application Ser. No. 12/630,458, filed Dec. 3, 2009. The entire contents of each of these patents and applications are incorporated herein by reference.

Throughout this application various publications are referenced. The disclosures of these publications in their entireties are hereby incorporated by reference into this application in order to describe more fully the state of the art to which this invention pertains.

TECHNICAL FIELD OF THE INVENTION

The present invention relates generally to detection and therapy of cancer. The invention is more specifically related to biomarkers, particularly apolipoprotein A-1 (ApoA-1) and variants thereof, and their use in treatment of women's cancers, particularly ovarian cancer as well as cervical cancer, endometrial cancer, and vulvar cancer. Molecules, including proteins, peptides, antibodies and antisense/interference nucleotides that modulate the expression and/or function of these targets can be used in vaccines and pharmaceutical compositions for the treatment of various cancers expressing the biomarkers identified herein, as well as in methods of detecting and assessing the malignancy of such cancers. The invention further provides methods for identifying molecules useful in the treatment and detection of cancer.

BACKGROUND OF THE INVENTION

Of the gynecologic malignancies, ovarian cancer has the highest mortality rate. Ovarian cancer often eludes the clinician because of the lack of early symptoms and signs. Hence, ovarian cancer tends to present at a late clinical stage in >85% of patients and is often followed by the emergence and outgrowth of chemotherapy-resistant disease in these patients after conventional primary cytoreductive surgery and induction chemotherapy. The American Cancer Society reported that >23,000 women were diagnosed with ovarian cancer in the United States in 2002, and 60% of those diagnosed, ≈14,000, are projected to die of their disease. More women die from ovarian cancer than from all other gynecologic malignancies combined. However, the 5-year survival rate for patients diagnosed with early-stage disease is often >90%, but it is <20% for advanced-stage disease, underscoring the importance of early detection.

The diagnostic and prognostic tumor biomarkers in use today are not adequate in distinguishing benign from malignant ovarian neoplasia and cannot differentiate among the various histological and clinically aggressive forms of ovarian cancer. The most commonly used biomarker for clinical screening and prognosis in patients with ovarian cancer is ovarian cancer antigen 125 (CA125). Serum CA125 levels are elevated in ≈80% of patients with advanced-stage epithelial ovarian cancer but are increased in only 50-60% of patients with early-stage disease. Serum CA125 levels may be falsely elevated in women with any i.p. pathology resulting in irritation of the serosa of the peritoneum or pericardium, uterine fibroids, renal disorders, and normal menses. Moreover, serum CA125 levels do not predict the outcome of cytoreductive surgery in patients with advanced epithelial ovarian cancer.

There remains a need for improved tools to permit the early detection and prognosis of cancer, particularly ovarian cancer. There also remains a need for targets useful in the detection and treatment of cancer.

SUMMARY OF THE INVENTION

The invention meets these needs and others by providing materials and methods for the treatment and detection of cancer. The present invention identifies multiple biomarker proteins that can be used in the diagnosis of early-stage ovarian cancer (OC), and one marker in particular, apolipoprotein A-1 (ApoA-1 or ApoA-I), that is shown to be useful as a target for cancer therapy. In a typical embodiment, the invention provides a therapeutic composition that comprises ApoA-1 or a variant thereof. In one embodiment, the variant shares at least 90% identity, preferably 95% identity, or 98% identity, with native ApoA-1 (SEQ ID NO: 1 or 3). One example of a variant of ApoA-1 is ApoA-1 Milano (SEQ ID NO: 2).

The methods provided by the invention include a method for inhibiting proliferation of cancer cells comprising contacting a cancer cell with a molecule that disrupts or modulates the biological activity of an OC molecule. Typically, the biological activity comprises specific binding of OC to an OC antibody or expression of an OC polynucleotide. Other methods provided include a method for treating cancer in a subject by administering to the subject a molecule that disrupts or modulates the biological activity of an OC molecule, a method for detecting cancer, and a method for identifying a cancer that is malignant. In one embodiment, the OC molecule is ApoA-1 and the modulating comprises delivering ApoA-1 or a variant thereof to the subject, contacting the ApoA-1 or variant thereof with the cancer cell, and/or effecting the expression or overexpression of ApoA-1.

Thus, in one embodiment, the invention provides a method of inhibiting the proliferation of gynecologic cancer cells, wherein the method comprises contacting the cancer cells with apolipoprotein A-1 (ApoA-1) or a variant thereof, wherein the variant shares at least 95% identity with native ApoA-1. In some embodiments, the variant shares at least 98% identity with native ApoA-1. In one embodiment, the variant is ApoA-1 Milano. The contacting can occur in vitro or in vivo.

In another embodiment, the invention provides a method of inhibiting tumor growth in a subject having gynecologic neoplasia. The method comprises administering to the subject an effective amount of ApoA-1 or a variant thereof, wherein the variant shares at least 95% identity with native ApoA-1 and, optionally, a pharmaceutical excipient. In a further embodiment, the invention provides a method of treating gynecologic cancer in a subject, the method comprising administering to the subject an effective amount of ApoA-1 or a variant thereof, wherein the variant shares at least 95% identity with native ApoA-1 and, optionally, a pharmaceutical excipient.

In the methods of the invention, the gynecological cancer may be ovarian, endometrial, cervical, vaginal or vulvar cancer. The ApoA-1 may, optionally, be administered as high-density lipoprotein (HDL), or as recombinant ApoA-1. The ApoA-1 may be administered transdermally, intravenously, intraperitoneally, subcutaneously, or intradermally. In a typical embodiment, the subject is mammalian. In one embodiment, the subject is human.

In addition, the invention provides ovarian cancer (OC) related molecules, compositions and additional kits comprising OC related molecules, and methods of using OC related molecules for the treatment and detection of cancer. In one embodiment, the invention provides an expression vector comprising a nucleic acid molecule that encodes an OC protein operably linked to an expression control sequence. The nucleic acid molecule may encode the OC protein in a sense or anti-sense orientation, depending on the intended use. Also provided are host cells containing such expression vectors, which can be used for the production of OC related molecules. In some embodiments, the nucleic acid molecule is labeled with a detectable marker, or provided in a composition with a pharmaceutically acceptable carrier.

The invention additionally provides OC polypeptides, including immunogenic OC peptides. In a typical embodiment, the OC polypeptide is ApoA-1 or a variant thereof. The OC polypeptide may be provided in a variety of forms, as appropriate for a particular use, including, for example, in a soluble form, immobilized on a substrate, or in combination with a pharmaceutically acceptable carrier or excipient. Antibodies directed against such OC polypeptides are also provided. In some embodiments, the antibody is labeled with a detectable marker, or provided in a composition with a pharmaceutically acceptable carrier.

Typically, the ApoA-1 is full-length (e.g., SEQ ID NO: 1-3) and unmodified. While ApoA-1 peptides, and particularly ApoA-1 mimetic peptides have been developed in efforts to identify molecules having similar function and/or ease of productive compared to full-length ApoA-1 protein for some areas of use, the modifications of these mimetic peptides (e.g., alpha-helical peptides) have rendered them entirely different from natural ApoA-1; in fact, the mimetic peptides share no structural similarity with the full length ApoA-1 protein molecule. Moreover, in the area of cardiovascular treatment, the mimetic peptides have been less effective and require such large quantities that therapeutic use of these peptides is impractical. Interestingly, the term mimetic peptide is a term developed over 2 decades ago that refers to an attempt to identify structurally dissimilar molecules that may share some functional properties with the full-length Apoa-1 protein; and in fact, no structural similarities exist between these alpha-helical peptides and the full-length Apoa-1 molecule. Hence, the term "mimetic peptide" is a misnomer, since the ApoA-1 full length protein shares nothing structurally in common with its mimetic peptides. The ApoA-1 mimetic peptides attempt only to mimic some of the features of the ApoA-1 full length protein function.

DETAILED DESCRIPTION OF THE INVENTION

The present invention is based on the discovery of biomarker proteins, namely ApoA-1, that can be used in the diagnosis and treatment of gynecologic cancers, including ovarian cancer. The biomarkers not only permit the distinction of patients with ovarian neoplasia (benign or malignant) from normal subjects, but they also allow the identification and distinction of patients with early-stage (stage I/II) ovarian cancer from those patients with benign ovarian tumors or normal individuals.

DEFINITIONS

All scientific and technical terms used in this application have meanings commonly used in the art unless otherwise specified. As used in this application, the following words or phrases have the meanings specified.

As used herein, "OC" refers to ovarian cancer.

As used herein, "OC related molecule" or "OC biomarker" refers to any one, alone or in combination with other, of the novel biomarkers or a novel panel of biomarkers identified herein as associated with ovarian cancer and described in U.S. Pat. No. 7,670,792. A biomarker is associated with ovarian cancer if its level (amount of molecule present) is up-regulated or down-regulated in neoplastic versus normal tissue or in malignant versus non-malignant tissue.

Figure 1:
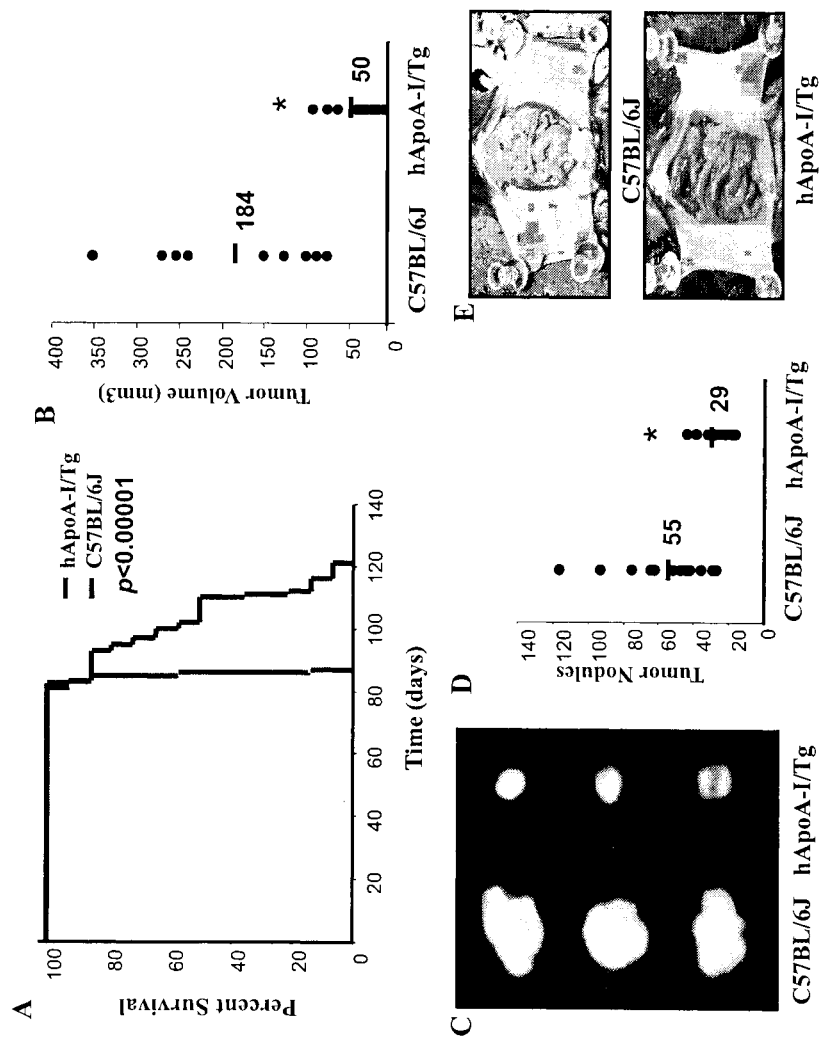
FIG. 1: Improved survival and significantly decreased tumor size in hApoA-I/Tg mice after injection of ID8 cells. (a) Wild-type C57BL/6J and hApoA-I/Tg mice on C57BL/6J background (n=14 per group, 9 weeks of age) were given an i.p. injection of ID8 cells ($8 \times 10^6$ cells per mouse) on day 1. The curves represent the percent of live mice on the days indicated. (b) Flank tumors were established in wild-type C57BL/6J (n=9) and hApoA-I/Tg female mice on C57BL/6J background (n=10) as described under Materials and Methods in Example 4. Mice were sacrificed 5 weeks after flank injection and tumor volumes were calculated by the formula $V=1/2(LXW2)$, where L is length (longest dimension) and W is width (shortest dimension). (c) Representative tumors from the two groups are shown. (d) Wild-type C57BL/6J and hApoA-I/Tg mice on a C57BL/6J background (n=13, eight weeks of age) were injected with ID8 cells by i.p. injection ($8 \times 10^6$ cells per mouse) and tumor burden was analyzed after nine weeks. Average tumor nodules on liver, spleen, kidney, diaphragm and intestines, were counted for each mouse and data from each group was combined and analyzed. (e) Representative mice from the two groups showing the tumor nodules on the peritoneal membranes. * Denotes $p<0.01$.

As used herein, "OC biomarker pattern of expression" refers to a pattern of protein expression substantially similar to that shown in FIG. 1 of U.S. Pat. No. 7,670,792 as "CANCER"; or the pattern shown in FIG. 7 therein as "Early Stage" or "Late Stage". This pattern of expression can be detected by any of the methods described therein.

As used herein, "biological activity of OC" refers to the specific binding of OC to an OC binding partner, such as an OC receptor or antibody, to the expression of an OC polynucleotide, and to the growth regulatory effects of OC related molecules.

As used here, "m/z" or "m/z ratio" refers to mass-to-charge ratio, as determined by the SELDI-mass spectroscopy protocol described in U.S. patent publication number 2005/0059013 (Mar. 17, 2005). The masses for the biomarkers described herein are considered accurate to within 0.15 percent of the specified value. Assigned m/z ratios are based on the identification of peaks in the spectrum that represent the signal generated by an analyte. Although peak selection can be done by eye, software is typically used to automate the detection of peaks (Ciphergen's ProteinChip® software). In general, this software functions by identifying signals having a signal-to-noise ratio above a selected threshold and labeling the mass of the peak at the center of the peak signal. One version of this software clusters all peaks appearing in the various spectra within a defined mass range, and assigns a mass (m/z) to all the peaks that are near the mid-point of the mass (m/z) cluster.

As used herein, "ApoA-1 related molecule" includes ApoA-1 polypeptides, polynucleotides encoding ApoA-1 polypeptides, polynucleotides complementary to those encoding ApoA-1 polypeptides, and antibodies that specifically recognize and bind ApoA-1 polypeptides.

As used herein, "polypeptide" includes proteins, fragments of proteins, and peptides, whether isolated from natural sources, produced by recombinant techniques or chemically synthesized. Polypeptides of the invention typically comprise at least about 6 amino acids.

As used herein, "tumor protein" is a protein that is expressed by tumor cells. Proteins that are tumor proteins also react detectably within an immunoassay (such as an ELISA) with antisera from a patient with cancer.

An "immunogenic polypeptide," as used herein is a portion of a protein that is recognized (i.e., specifically bound) by a B-cell and/or T-cell surface antigen receptor. Such immunogenic polypeptides generally comprise at least 5 amino acid residues, more preferably at least 10, and still more preferably at least 20 amino acid residues of a protein associated with cancer or infectious disease. Certain preferred immunogenic polypeptides include peptides in which an N-terminal leader sequence and/or transmembrane domain have been deleted. Other preferred immunogenic polypeptides may contain a small N- and/or C-terminal deletion (e.g., 1-30 amino acids, preferably 5-15 amino acids), relative to the mature protein.

As used herein, "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

The term "nucleic acid" or "polynucleotide" refers to a deoxyribonucleotide or ribonucleotide polymer in either single- or double-stranded form, and unless otherwise limited, encompasses known analogs of natural nucleotides that hybridize to nucleic acids in a manner similar to naturally-occurring nucleotides.

As used herein, "antigen-presenting cell" or "APC" means a cell capable of handling and presenting antigen to a lymphocyte. Examples of APCs include, but are not limited to, macrophages, Langerhans-dendritic cells, follicular dendritic cells, B cells, monocytes, fibroblasts and fibrocytes. Dendritic cells are a preferred type of antigen presenting cell. Dendritic cells are found in many non-lymphoid tissues but can migrate via the afferent lymph or the blood stream to the T-dependent areas of lymphoid organs. In non-lymphoid organs, dendritic cells include Langerhans cells and interstitial dendritic cells. In the lymph and blood, they include afferent lymph veiled cells and blood dendritic cells, respectively. In lymphoid organs, they include lymphoid dendritic cells and interdigitating cells.

As used herein, "modified" to present an epitope refers to antigen-presenting cells (APCs) that have been manipulated to present an epitope by natural or recombinant methods. For example, the APCs can be modified by exposure to the isolated antigen, alone or as part of a mixture, peptide loading, or by genetically modifying the APC to express a polypeptide that includes one or more epitopes.

As used herein, "pharmaceutically acceptable carrier" or "excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline.

Compositions comprising such carriers are formulated by well known conventional methods (see, for example, *Remington's Pharmaceutical Sciences,* 18th edition, A. Gennaro, ed., Mack Publishing Co., Easton, Pa., 1990).

As used herein, "a" or "an" means at least one, unless clearly indicated otherwise.

Polynucleotides of the Invention

The invention provides polynucleotides that encode one or more OC polypeptides, specifically including those encoding ApoA-1 or a portion or variant thereof. Preferred polynucleotides comprise at least 15 consecutive nucleotides, preferably at least 30 consecutive nucleotides and more preferably at least 45 consecutive nucleotides, that encode an OC polypeptide. Polynucleotides that are fully complementary to any such sequences are also encompassed by the present invention. Polynucleotides may be single-stranded (coding or antisense) or double-stranded, and may be DNA (genomic, cDNA or synthetic) or RNA molecules, including siRNA. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials. Portions of such OC polynucleotides can be useful as primers and probes for the amplification and detection of OC related molecules in tissue specimens. Polynucleotides may comprise a native sequence (i.e., an endogenous sequence that encodes an OC polypeptide or a portion thereof) or may comprise a variant of such a sequence. Polynucleotide variants contain one or more substitutions, additions, deletions and/or insertions such that the immunogenicity of the encoded polypeptide is not diminished, relative to a native OC protein. Variants preferably exhibit at least about 70% identity, more preferably at least about 80% identity and most preferably at least about 90% identity to a polynucleotide sequence that encodes a native OC protein or a portion thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 Methods in Enzymology vol. 183, Academic Press, Inc., San Diego, Calif.; Higgins, D. G. and Sharp, P. M. (1989) CABIOS 5:151-153; Myers, E. W. and Muller W. (1988) CABIOS 4:11-17; Robinson, E. D. (1971) Comb. Theor. 11:105; Santou, N., Nes, M. (1987) Mol. Biol. Evol. 4:406-425; Sneath, P. H. A. and Sokal, R. R. (1973) Numerical Taxonomy the Principles and Practice of Numerical Taxonomy, Freeman Press, San Francisco, Calif.; Wilbur, W. J. and Lipman, D. J. (1983) Proc. Natl. Acad. Sci. USA 80:726-730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native OC protein (or a complementary sequence).

Suitable "moderately stringent conditions" include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Polynucleotides may be prepared using any of a variety of techniques known in the art. DNA encoding an OC protein may be obtained from a cDNA library prepared from tissue expressing an OC protein mRNA. Accordingly, human OC DNA can be conveniently obtained from a cDNA library prepared from human tissue. The OC protein-encoding gene may also be obtained from a genomic library or by oligonucleotide synthesis. Libraries can be screened with probes (such as antibodies to OC or oligonucleotides of at least about 20-80 bases) designed to identify the gene of interest or the protein encoded by it. Screening the cDNA or genomic library with the selected probe may be conducted using standard procedures, such as those described in Sambrook et al., *Molecular Cloning: A Laboratory Manual* (New York: Cold Spring Harbor Laboratory Press, 1989). An alternative means to isolate the gene encoding OC is to use PCR methodology (Sambrook et al., supra; Dieffenbach et al., *PCR Primer: A Laboratory Manual* (Cold Spring Harbor Laboratory Press, 1995)).

The oligonucleotide sequences selected as probes should be sufficiently long and sufficiently unambiguous that false positives are minimized. The oligonucleotide is preferably labeled such that it can be detected upon hybridization to DNA in the library being screened. Methods of labeling are well known in the art, and include the use of radiolabels, such as $^{32}$P-labeled ATP, biotinylation or enzyme labeling. Hybridization conditions, including moderate stringency and high stringency, are provided in Sambrook et al., supra.

Polynucleotide variants may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis (see Adelman et al., DNA 2:183, 1983). Alternatively, RNA molecules may be generated by in vitro or in vivo transcription of DNA sequences encoding an OC protein, or portion thereof, provided that the DNA is incorporated into a vector with a suitable RNA polymerase promoter (such as T7 or SP6). Certain portions may be used to prepare an encoded polypeptide, as described herein. In addition, or alternatively, a portion may be administered to a patient such that the encoded polypeptide is generated in vivo (e.g., by transfecting antigen-presenting cells, such as dendritic cells, with a cDNA construct encoding an OC polypeptide, and administering the transfected cells to the patient).

Any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl-methyl-, thio- and other modified forms of adenine, cytidine, guanine, thymine and uridine.

Nucleotide sequences can be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

Within certain embodiments, polynucleotides may be formulated so as to permit entry into a cell of a mammal, and to permit expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g., avian pox virus). Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art.

Other formulations for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Antisense Molecules

The antisense molecules of the present invention comprise a sequence substantially complementary, or preferably fully complementary, to all or a fragment of an OC gene. Included are fragments of oligonucleotides within the coding sequence of an OC gene. Antisense oligonucleotides of DNA or RNA complementary to sequences at the boundary between introns and exons can be employed to prevent the maturation of newly-generated nuclear RNA transcripts of specific genes into mRNA for transcription. Antisense RNA complimentary to specific genes can hybridize with the mRNA for that gene and prevent its translation. The antisense molecule can be DNA, RNA, or a derivative or hybrid thereof. Examples of such derivative molecules include, but are not limited to, peptide nucleic acid (PNA) and phosphorothioate-based molecules such as deoxyribonucleic guanidine (DNG) or ribonucleic guanidine (RNG).

Antisense RNA can be provided to the cell as "ready-to-use" RNA synthesized in vitro or as an antisense gene stably transfected into cells which will yield antisense RNA upon transcription. Hybridization with mRNA results in degradation of the hybridized molecule by RNAse H and/or inhibition of the formation of translation complexes. Both result in a failure to produce the product of the original gene.

Both antisense RNA and DNA molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro or in vivo transcription of DNA sequences encoding the antisense RNA molecule. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

DNA molecules may be modified to increase intracellular stability and half-life. Possible modifications include, but are not limited to, the addition of flanking sequences of the 5' and/or 3' ends of the molecule or the use of phosphorothioate or 2' O-methyl rather than phosphodiesterase linkages within the backbone of the molecule. Other modifications include the use of chimeric antisense compounds. Chimeric antisense compounds of the invention may be formed as composite structures of two or more oligonucleotides, modified oligonucleotides, oligonucleosides and/or oligonucleotide mimetics. Such compounds have also been referred to in the art as hybrids or gapmers. Representative United States patents that teach the preparation of such hybrid structures include, but are not limited to, U.S. Pat. Nos. 5,700,922 and 6,277,603.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Antisense compositions of the invention include oligonucleotides formed of homopyrimidines that can recognize local stretches of homopurines in the DNA double helix and bind to them in the major groove to form a triple helix. See: Helen, C and Toulme, J J. Specific regulation of gene expression by antisense, sense, and antigene nucleic acids. Biochem. Biophys Acta, 1049:99-125, 1990. Formation of the triple helix would interrupt the ability of the specific gene to undergo transcription by RNA polymerase. Triple helix formation using myc-specific oligonucleotides has been observed. See: Cooney, M, et al. Science 241:456-459.

Antisense sequences of DNA or RNA can be delivered to cells. Several chemical modifications have been developed to prolong the stability and improve the function of these molecules without interfering with their ability to recognize specific sequences. These include increasing their resistance to degradation by DNases, including phosphotriesters, methylphosphonates, phosphorothioates, alpha-anomers, increasing their affinity for binding partners by covalent linkage to various intercalating agents such as psoralens, and increasing uptake by cells by conjugation to various groups including polylysine. These molecules recognize specific sequences encoded in mRNA and their hybridization prevents translation of and increases the degradation of these messages.

Antisense compositions including oligonucleotides, derivatives and analogs thereof, conjugation protocols, and antisense strategies for inhibition of transcription and translation are generally described in: Antisense Research and Applications, Crooke, S. and B. Lebleu, eds. CRC Press, Inc. Boca Raton Fla. 1993; Nucleic Acids in Chemistry and Biology Blackburn, G. and M. J. Gait, eds. IRL Press at Oxford University Press, Inc. New York 1990; and Oligonucleotides and Analogues: A Practical Approach Eckstein, F. ed., IRL Press at Oxford University Press, Inc. New York 1991; which are each hereby incorporated herein by reference including all references cited therein which are hereby incorporated herein by reference.

RNA Interference

Long double-stranded RNAs (dsRNAs; typically >200 nt) can be used to silence the expression of a target gene. The dsRNAs enter a cellular pathway that is commonly referred to as the RNA interference (RNAi) pathway. First, the dsRNAs get processed into 20-25 nucleotide (nt) small interfering RNAs (siRNAs) by an RNase III-like enzyme called Dicer (initiation step). Then, the siRNAs assemble into endoribonuclease-containing complexes known as RNA-induced silencing complexes (RISCs), unwinding in the process. The siRNA strands subsequently guide the RISCs to complementary RNA molecules, where they cleave and destroy the cognate RNA (effecter step). Cleavage of cognate RNA takes place near the middle of the region bound by the siRNA strand.

In mammalian cells, introduction of long dsRNA (>30 nt) initiates a potent antiviral response, exemplified by nonspecific inhibition of protein synthesis and RNA degradation. The mammalian antiviral response can be bypassed, however, by the introduction or expression of siRNAs (Ambion, Inc., Austin, Tex.).

Apolipoprotein-A1 (ApoA-1)

The ApoA-1 to be used in methods of the invention is typically native ApoA-1 or a variant thereof. Variants typically share at least about 95% identity in amino acid sequence with native ApoA-1, over the length of the native mature ApoA-1 protein (SEQ ID NO: 1).

The amino acid sequence of native mature human ApoA-1 is shown in SEQ ID NO: 1:

deppqspwdrvkdlatvyvdvlkdsgrdyvsqfegsalgkqlnlklldnwdsvtstfsklreqlgp vtqefwdnleketeglrqemskdleevkakvqpylddfqkkwqeemelyrqkveplraelqegarqklhe lqeklsplgeemrdrarahvdalrthlapysdelrqrlaarlealkenggarlaeyhakatehlstlsek akpaledlrqgllpvlesfkvsflsaleeytkklntq The amino acid sequence of the naturally-occurring variant of mature human ApoA-1, known as ApoA-1-Milano, has a cysteine in place of an arginine at position 197 (173 of the mature form), as shown in SEQ ID NO: 2:

```
deppqspwdrvkdlatvyvdvlkdsgrdyvsqfegsalgkqlnlklldnwdsvtstfsklreqlgp vtqefwdnleketeglrqemskdleevkakvqpylddfqkkwqeemelyrqkveplraelqegarqklhe lqeklsplgeemrdrarahvdalrthlapysdelrqclaarlealkenggarlaeyhakatehlstlsek akpaledlrqgllpvlesfkvsflsaleeytkklntq
```

The complete amino acid sequence of native human ApoA-1, including the signal peptide (aa 1-18) and propro-tein, is described in the NCBI database, Accession No. NP_000030, as:

```
                                                      (SEQ ID NO: 3)
  1 mkaavltlav lfltgsqarh fwqqdeppqs pwdrvkdlat vyvdvlkdsg rdyvsqfegs 61 algkqlnlkl ldnwdsvtst fsklreqlgp vtqefwdnle keteglrqem skdleevkak 121 vqpylddfqk kwqeemelyr qkveplrael qegarqklhe lqeklsplge emrdrarahv 181 dalrthlapy sdelrqrlaa rlealkengg arlaeyhaka tehlstlsek akpaledlrq 241 gllpvlesfk vsflsaleey tkklntq
```

ApoA-1 polypeptides as described herein may be of any length. Exemplary lengths include, but are not limited to, up to 25, 50, 100, 150, 175, 200, 225, 250 amino acids or more. Typically, the ApoA-1 polypeptide retains at least 90% identity with the 243 amino acid sequence of native mature ApoA-1 shown in SEQ ID NO: 1. In some embodiments, the ApoA-1 polypeptide retains at least 95%, or in some embodiments, at least 98%, identity with the amino acid sequence of SEQ ID NO: 1, over the entire length of SEQ ID NO: 1.

Additional sequences derived from the native protein and/or heterologous sequences may be present, and such sequences may, but need not, possess further ligand binding, immunogenic or other biologic properties. Those skilled in the art will appreciate that other portions or variants thereof will be useful in the treatment of cancer.

A variant polypeptide of the invention, as used herein, is a polypeptide that differs from a native protein in one or more substitutions, deletions, additions and/or insertions, such that the immunogenicity or binding affinity for a binding partner of the polypeptide is not substantially diminished. In other words, the ability of a variant to bind its binding partner may be enhanced or unchanged, relative to the native protein, or may be diminished by less than 50%, and preferably less than 20%, relative to the native protein. Such variants may generally be identified by modifying one of the above polypeptide sequences and evaluating the reactivity of the modified polypeptide with a known binding partner or antigen-specific antibodies or antisera as described. Some variants include those in which one or more portions, such as an N-terminal leader sequence, have been removed. Other preferred variants include variants in which a small portion (e.g., 1-30 amino acids, preferably 5-15 amino acids) has been removed from the N- and/or C-terminal of the mature protein. Polypeptide variants preferably exhibit at least about 90%, more preferably at least about 95% and most preferably at least about 98% identity (determined as described above) to the identified polypeptides.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

Polypeptides may comprise a signal (or leader) sequence at the N-terminal end of the protein that co-translationally or post-translationally directs transfer of the protein. The polypeptide may also be conjugated to a linker or other sequence for ease of synthesis, purification or identification of the polypeptide (e.g., poly-FEs), or to enhance binding of the polypeptide to a solid support. For example, a polypeptide may be conjugated to an immunoglobulin Fc region.

Recombinant polypeptides encoded by DNA sequences as described above may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, yeast, insect cells or a mammalian cell line such as COS or CHO. Supernatants from suitable host/vector systems that secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Portions and other variants may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, J. Am. Chem. Soc. 85:2149-2146, 1963. Equipment for automated synthesis of polypeptides is commercially available from suppliers such as Perkin Elmer/Applied BioSystems Division (Foster City, Calif.), and may be operated according to the manufacturer's instructions.

Polypeptides can be synthesized on a Perkin Elmer/Applied Biosystems Division 430A peptide synthesizer using FMOC chemistry with HPTU (O-BenzotriazoleN,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%-60% acetonitrile (containing 0.1% TFA) in water may be used to elute the peptides. Following lyophilization of the pure fractions, the peptides may be characterized using electrospray or other types of mass spectrometry and by amino acid analysis.

Fusion Proteins

In some embodiments, the polypeptide is a fusion protein that comprises multiple polypeptides as described herein, or that comprises at least one polypeptide as described herein and an unrelated sequence. In some embodiments, the fusion protein comprises an ApoA-1 polypeptide and an immunogenic polypeptide. The immunogenic polypeptide can comprise, for example, all or a portion of an additional tumor protein.

Additional fusion partners can be added. A fusion partner may, for example, serve as an immunological fusion partner by assisting in the provision of T helper epitopes, preferably T helper epitopes recognized by humans. As another example, a fusion partner may serve as an expression enhancer, assisting in expressing the protein at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and the second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., Gene 40:39-46, 1985; Murphy et al., Proc. Natl. Acad. Sci. USA 83:8258-8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located 5' to the DNA sequence encoding the first polypeptides. Similarly, stop codons required to end translation and transcription termination signals are present 3' to the DNA sequence encoding the second polypeptide.

Fusion proteins are also provided that comprise a polypeptide of the present invention together with an unrelated immunogenic protein. Preferably the immunogenic protein is capable of eliciting a memory response. Examples of such proteins include tetanus, tuberculosis and hepatitis proteins (see, for example, Stoute et al., New Engl. J. Med. 336:86-91, 1997).

Within preferred embodiments, an immunological fusion partner is derived from protein D, a surface protein of the gram-negative bacterium Haemophilus influenza B (WO 91/18926). Preferably, a protein D derivative comprises approximately the first third of the protein (e.g., the first N-terminal 100-110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS I (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; Gene 43:265-292, 1986). LYTA is an autolysin that specifically degrades certain bonds in the peptidoglycan backbone. The C-terminal domain of the LYTA protein is responsible for the affinity to the choline or to some choline analogues such as DEAR This property has been exploited for the development of *E. coli* C-LYTA expressing plasmids useful for expression of fusion proteins. Purification of hybrid proteins containing the C-LYTA fragment at the amino terminus has been described (see Biotechnology 10:795-798, 1992). Within a preferred embodiment, a repeat portion of LYTA may be incorporated into a fusion protein. A repeat portion is found in the C-terminal region starting at residue 178. A particularly preferred repeat portion incorporates residues 188-305.

In general, polypeptides (including fusion proteins) and polynucleotides as described herein are isolated. An "isolated" polypeptide or polynucleotide is one that is removed from its original environment. For example, a naturally occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Pharmaceutical Compositions and Vaccines

The invention provides ApoA-1 polypeptides, polynucleotides, and/or related molecules that are incorporated into pharmaceutical compositions, including immunogenic compositions (i.e., vaccines). In a typical embodiment, the ApoA-1 polypeptide has the amino acid sequence shown in SEQ ID NO: 1 or a variant thereof, such as that shown in SEQ ID NO: 2. As is understood in the art, ApoA-1 is a significant component of high-density lipoprotein (HDL). Accordingly, one can administer ApoA-1 by administering HDL as well as by administering the complete ApoA-1 protein shown in SEQ ID NO: 3, with or without the signal peptide (aa 1-18).

Pharmaceutical compositions comprise one or more such compounds and, optionally, a physiologically acceptable carrier. Administration of ApoA-1 is facilitated by preparation with inert lipids, e.g. to form micelles. In a typical embodiment, ApoA-1 is administered transdermally, such as via a patch adhered to the subject's skin.

While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous, intradermal, transdermal or intramuscular administration. For parenteral administration, such as subcutaneous injection, the carrier preferably comprises a fat, and optionally water, saline, alcohol, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention.

In addition, the carrier may contain other pharmacologically-acceptable excipients for modifying or maintaining the pH, osmolarity, viscosity, clarity, color, sterility, stability, rate of dissolution, or odor of the formulation. Similarly, the carrier may contain still other pharmacologically-acceptable excipients for modifying or maintaining the stability, rate of dissolution, release, or absorption or penetration across the blood-brain barrier of the molecule. Such excipients are those substances usually and customarily employed to formulate dosages for parenteral administration in either unit dose or multi-dose form or for direct infusion into the CSF by continuous or periodic infusion from an implanted pump.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions of the present invention may be formulated as a lyophilizate. Compounds may also be encapsulated within liposomes using well known technology.

Vaccines may comprise one or more such compounds and an adjuvant that serves as a non-specific immune response enhancer. The adjuvant may be any substance that enhances an immune response to an exogenous antigen. Examples of adjuvants include conventional adjuvants, biodegradable microspheres (e.g., polylactic galactide), immunostimulatory oligonucleotides and liposomes (into which the compound is incorporated; see e.g., Fullerton, U.S. Pat. No. 4,235,877). Vaccine preparation is generally described in, for example, M. F. Powell and M. J. Newman, eds., "Vaccine Design (the subunit and adjuvant approach)," Plenum Press (NY, 1995). Pharmaceutical compositions and vaccines within the scope of the present invention may also contain other compounds that may be biologically active or inactive. For example, one or more immunogenic portions of other tumor antigens may be present, either incorporated into a fusion polypeptide or as a separate compound, within the composition or vaccine.

A pharmaceutical composition or vaccine can contain DNA encoding one or more of the polypeptides as described above, such that the polypeptide is generated in situ. As noted above, the DNA may be present within any of a variety of delivery systems known to those of ordinary skill in the art, including nucleic acid expression systems, bacteria and viral expression systems. Numerous gene delivery techniques are well known in the art, such as those described by Rolland, Crit. Rev. Therap. Drug Carrier Systems 15:143-198, 1998, and references cited therein. Appropriate nucleic acid expression systems contain the necessary DNA sequences for expression in the patient (such as a suitable promoter and terminating signal). Bacterial delivery systems involve the administration of a bacterium (such as *Bacillus-Calmette-Guerrin*) that expresses an immunogenic portion of the polypeptide on its cell surface or secretes such an epitope.

In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., Proc. Natl. Acad. Sci. USA 86:317-321, 1989; Flexner et al., Ann. N.Y. Acad Sci. 569:86-103, 1989; Flexner et al., Vaccine 8:17-21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner-Biotechniques 6:616-627, 1988; Rosenfeld et al., Science 252:431-434, 1991; Kolls et al., Proc. Natl. Acad. Sci. USA 91:215-219, 1994; Kass-Eisler et al., Proc. Natl. Acad. Sci. USA 90:11498-11502, 1993; Guzman et al., Circulation 88:2838-2848, 1993; and Guzman et al., Cir. Res. 73:1202-1207, 1993. Techniques for incorporating DNA into such expression systems are well known to those of ordinary skill in the art. The DNA may also be "naked," as described, for example, in Ulmer et al., Science 259:1745-1749, 1993 and reviewed by Cohen, Science 259:1691-1692, 1993. The uptake of naked DNA may be increased by coating the DNA onto biodegradable beads, which are efficiently transported into the cells.

Any of a variety of adjuvants may be employed in the vaccines of this invention. Most adjuvants contain a substance designed to protect the antigen from rapid catabolism, such as aluminum hydroxide or mineral oil, and a stimulator of immune responses, such as lipid A, Bortadella pertussis or Mycobacterium tuberculosis derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); aluminum salts such as aluminum hydroxide gel (alum) or aluminum phosphate; salts of calcium, iron or zinc; an insoluble suspension of acylated tyrosine acylated sugars; cationically or anionically derivatized polysaccharides; polyphosphazenes biodegradable microspheres; monophosphoryl lipid A and quil A. Cytokines, such as GM CSF or interleukin-2, -7, or -12, may also be used as adjuvants.

Within the vaccines provided herein, the adjuvant composition is preferably designed to induce an immune response predominantly of the Th1 type. High levels of Th1-type cytokines (e.g., IFN-$\alpha$, IL-2 and IL-12) tend to favor the induction of cell mediated immune responses to an administered antigen. In contrast, high levels of Th2-type cytokines (e.g., IL-4, IL-5, IL-6, IL-10 and TNF-$\beta$) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, Ann. Rev. Immunol. 7:145-173, 1989.

The compositions described herein may be administered as part of a sustained release formulation (i.e., a formulation such as a capsule or sponge that effects a slow release of compound following administration). Such formulations may generally be prepared using well known technology and administered by, for example, oral, rectal or subcutaneous implantation, or by implantation at the desired target site, such as a site of surgical excision of a tumor. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

Therapeutic and Prophylactic Methods

Treatment includes prophylaxis and therapy. Prophylaxis or therapy can be accomplished by a single direct injection at a single time point or multiple time points to a single or multiple sites. Administration can also be nearly simultaneous to multiple sites. Patients or subjects include mammals, such as human, bovine, equine, canine, feline, porcine, and ovine animals. The subject is preferably a human. In a typical embodiment, treatment comprises administering to a subject ApoA-1 or a variant thereof.

A cancer may be diagnosed using criteria generally accepted in the art, including the presence of a malignant tumor. Pharmaceutical compositions and vaccines may be administered either prior to or following surgical removal of primary tumors and/or treatment such as administration of radiotherapy or conventional chemotherapeutic drugs.

Within certain embodiments, immunotherapy may be active immunotherapy, in which treatment relies on the in vivo stimulation of the endogenous host immune system to react against tumors or infected cells with the administration of immune response-modifying agents (such as polypeptides and polynucleotides disclosed herein). Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T cells as discussed above, T lymphocytes (such as CD8+ cytotoxic T lymphocytes and CD4+ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. In a preferred embodiment, dendritic cells are modified in vitro to present the polypeptide, and these modified APCs are administered to the subject. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Administration and Dosage

The compositions are administered in any suitable manner, often with pharmaceutically acceptable carriers. Suitable methods of administering cells in the context of the present invention to a subject are available, and, although more than one route can be used to administer a particular cell composition, a particular route can often provide a more immediate and more effective reaction than another route.

The dose administered to a patient, in the context of the present invention, should be sufficient to effect a beneficial therapeutic response in the patient over time, or to inhibit disease progression. Thus, the composition is administered to a subject in an amount sufficient to elicit an effective immune response to the specific antigens and/or to alleviate, reduce, cure or at least partially arrest symptoms and/or complications from the disease. An amount adequate to accomplish this is defined as a "therapeutically effective dose."

Routes and frequency of administration of the therapeutic compositions disclosed herein, as well as dosage, will vary from individual to individual, and may be readily established using standard techniques. In general, the pharmaceutical compositions and vaccines may be administered, by injection (e.g., intracutaneous, intratumoral, intramuscular, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. In one embodiment, 2 intradermal injections of the composition are administered 10 days apart.

A suitable dose is an amount of a compound that, when administered as described above, is capable of promoting an anti-tumor immune response, and is at least 10-50% above the basal (i.e., untreated) level. Such response can be monitored, for example, by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to nonvaccinated patients. In general, for pharmaceutical compositions and vaccines comprising one or more polypeptides, the amount of each polypeptide present in a dose ranges from about 100 μg to 5 mg per kg of host. Suitable volumes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a tumor protein generally correlate with an improved clinical outcome. Such immune responses may generally be evaluated using standard proliferation, cytotoxicity or cytokine assays, which may be performed using samples obtained from a patient before and after treatment.

EXAMPLES

The following examples are presented to illustrate the present invention and to assist one of ordinary skill in making and using the same. The examples are not intended in any way to otherwise limit the scope of the invention.

Example 1

Identification of Biomarkers for Ovarian Cancer Using Strong Anion-Exchange ProteinChips This example demonstrates three ovarian cancer biomarker protein panels that, when used together, effectively distinguished serum samples from healthy controls and patients with either benign or malignant ovarian neoplasia. In summary, 184 serum samples from patients with ovarian cancer (n=109), patients with benign tumors (n=19), and healthy donors (n=56) were analyzed on strong anion-exchange surfaces using surface-enhanced laser desorption/ionization time-of-flight mass spectrometry technology. Univariate and multivariate statistical analyses applied to protein-profiling data obtained from 140 training serum samples identified three biomarker protein panels. The first panel of five candidate protein biomarkers, termed the screening biomarker panel, effectively diagnosed benign and malignant ovarian neoplasia (95.7% sensitivity, 82.6% specificity, 89.2% accuracy, and receiver operating characteristic (ROC) area under the curve of 0.94). The other two panels, consisting of five and four candidate protein biomarkers each, effectively distinguished between benign and malignant ovarian neoplasia and were therefore referred to as validation biomarker panel I (81.5% sensitivity, 94.9% specificity, 88.2% accuracy, and ROC=0.94) and validation biomarker panel II (72.8% sensitivity, 94.9% specificity, 83.9% accuracy, and ROC=0.90). The three ovarian cancer biomarker protein panels correctly diagnosed 41 of the 44 blinded test samples: 21 of 22 malignant ovarian neoplasias (10 of 11 early-stage ovarian cancer (I/II) and 11 of 11 advanced-stage ovarian cancer (III/IV)), 6 of 6 low malignant potential, 5 of the 6 benign tumors, and 9 of 10 normal patient samples.

The details of the materials, methods and results can be found in WO 2006/019906, published 23 Feb. 2006.

Example 2

Characterization of Ovarian Cancer Serum Biomarkers for Early Detection

This example demonstrates the identification, characterization, and validation of the proteins that represent the SELDI-TOF-MS peaks from the ovarian cancer biomarker panels. Mass spectrometry and other analytical methods were employed to identify proteins of interest in human serum. The Example describes the identity of proteins that represent the m/z peaks 12.9, 13.8, 15.1, 15.9, 28 and 78.9 kDa in the ovarian cancer biomarker panels. Using microliquid chromatography-tandem mass spectrometry, the following m/z peaks were identified as: transthyretin (TTR): 12.9 kDa and 13.9 kDa, hemoglobin, both alpha-hemoglobin (alpha-Hb): 15.1 kDa, and beta-hemoglobin (beta-Hb): 15.9 kDa, apolipoprotein A1 (ApoA1): 28 kDa and transferrin (TF): 78.9 kDa. Western and ELISA techniques (independent of SELDI) confirmed the differential expression of TTR, Hb and TF in a group of ovarian cancer serum samples. Multivariate analyses improved the detection of early stage ovarian tumors (low malignant potential and malignant) as compared to cancer antigen CA125 alone. Multivariate analysis with only the mucinous subtype of early stage ovarian tumors showed the marker to greatly improve the detection of disease as compared to CA125 alone.

The details of the materials, methods and results can be found in WO 2006/019906, published 23 Feb. 2006.

Example 3

Identification of Additional Ovarian Cancer Serum Biomarkers

This example demonstrates the identification of additional biomarkers from serum samples that exhibit sensitivity and specificity in detecting ovarian neoplasia. These biomarkers were identified using SELDI as described above. The following table lists the protein identity, m/z ratios (in Daltons, "Marker"), cut point, sensitivity ("Sens"), specificity ("Spec"), accuracy ("Acc") of each biomarker. Subsequent columns indicate the mean level observed for each biomarker in the screening (normal and neoplasm) and validation (nonmalignant and malignant) panels. N=140.

| | | | | | | Mean Level of Biomarker | | | |
| | | | | | | Screening | | Validation | |
| Protein | Marker | Cut Point | Sens | Spec | Acc | Normal | Neoplasm | Non-Malignant | Malignant |
| --- | --- | --- | --- | --- | --- | --- | --- | --- | --- |
| | M1953 | 1.18 | 0.70 | 0.63 | 0.67 | 1.57 | 4.25 | 2.95 | 3.67 |
| | M2065 | 1.70 | 0.63 | 0.70 | 0.66 | 1.73 | 3.23 | 2.63 | 2.81 |
| | M2216 | 0.87 | 0.65 | 0.63 | 0.64 | 1.04 | 2.60 | 1.81 | 2.30 |
| | M2928 | 1.35 | 0.55 | 0.83 | 0.69 | 0.79 | 2.06 | 1.38 | 1.84 |
| | M2937 | 1.79 | 0.69 | 0.72 | 0.70 | 1.81 | 3.35 | 2.14 | 3.36 |

-continued

| Protein | Marker | Cut Point | Sens | Spec | Acc | Mean Level of Biomarker | | | |
|---|---|---|---|---|---|---|---|---|---|
| | | | | | | Screening | | Validation | |
| | | | | | | Normal | Neoplasm | Non-Malignant | Malignant |
| | M3143 | 1.59 | 0.65 | 0.65 | 0.65 | 1.64 | 2.59 | 2.02 | 2.47 |
| | M3423 | 0.48 | 0.57 | 0.74 | 0.66 | 0.57 | 1.54 | 0.71 | 1.59 |
| | M3427 | 0.58 | 0.66 | 0.67 | 0.67 | 0.63 | 1.66 | 1.04 | 1.52 |
| | M4144 | 4.26 | 0.74 | 0.63 | 0.69 | 4.46 | 6.79 | 5.25 | 6.59 |
| | M4375 | 0.98 | 0.76 | 0.59 | 0.67 | 0.94 | 1.54 | 0.97 | 1.61 |
| | M4456 | 2.01 | 0.60 | 0.87 | 0.73 | 1.36 | 3.05 | 1.54 | 3.19 |
| | M4629 | 3.48 | 0.35 | 0.93 | 0.64 | 2.22 | 3.20 | 2.42 | 3.21 |
| | M5064 | 1.21 | 0.73 | 0.70 | 0.71 | 1.16 | 2.11 | 1.18 | 2.24 |
| | M6884 | 7.77 | 0.67 | 0.93 | 0.80 | 10.46 | 6.87 | 10.12 | 6.54 |
| | M6931 | 10.08 | 0.70 | 0.80 | 0.75 | 12.29 | 8.31 | 12.05 | 7.85 |
| | M7550 | 0.96 | 0.86 | 0.65 | 0.76 | 1.09 | 3.13 | 1.70 | 3.01 |
| | M7657 | 1.19 | 0.57 | 0.89 | 0.73 | 0.75 | 1.45 | 0.92 | 1.44 |
| | M7756 | 1.12 | 0.48 | 0.91 | 0.70 | 0.65 | 1.25 | 0.68 | 1.32 |
| | M8117 | 2.16 | 0.76 | 0.76 | 0.76 | 1.82 | 2.61 | 1.94 | 2.65 |
| | M10874 | 0.35 | 0.85 | 0.43 | 0.64 | 0.42 | 0.50 | 0.41 | 0.52 |
| | M12785 | 1.17 | 0.61 | 0.80 | 0.71 | 1.46 | 1.12 | 1.33 | 1.16 |
| TTR | M13797 | 22.73 | 0.74 | 0.91 | 0.83 | 27.77 | 18.72 | 26.53 | 18.17 |
| HBA | M15074 | 1.38 | 0.81 | 0.76 | 0.78 | 1.50 | 4.47 | 2.23 | 4.42 |
| HBB | M15850 | 1.29 | 0.67 | 0.83 | 0.75 | 1.08 | 4.09 | 1.83 | 4.02 |
| | M16850 | 0.24 | 0.59 | 0.91 | 0.75 | 0.12 | 0.33 | 0.15 | 0.35 |
| | M18559 | 0.29 | 0.60 | 0.72 | 0.66 | 0.27 | 0.45 | 0.25 | 0.49 |
| | M18912 | 0.07 | 0.63 | 0.76 | 0.69 | 0.05 | 0.13 | 0.06 | 0.13 |
| | M18980 | 0.08 | 0.49 | 0.78 | 0.64 | 0.05 | 0.10 | 0.05 | 0.10 |
| | M19186 | 0.10 | 0.33 | 1.00 | 0.66 | 0.03 | 0.07 | 0.03 | 0.08 |
| | M20989 | 0.66 | 0.66 | 0.85 | 0.75 | 0.77 | 0.63 | 0.74 | 0.63 |
| | M22959 | 1.15 | 0.70 | 0.85 | 0.77 | 1.06 | 1.39 | 1.08 | 1.43 |
| | M27595 | 0.50 | 0.73 | 0.89 | 0.81 | 0.91 | 0.41 | 0.83 | 0.39 |
| APOA1 | M27977 | 0.54 | 0.48 | 0.85 | 0.66 | 1.52 | 0.79 | 1.47 | 0.71 |
| | M29190 | 0.81 | 0.38 | 0.89 | 0.64 | 0.69 | 0.76 | 0.72 | 0.75 |
| | M29512 | 0.68 | 0.68 | 0.67 | 0.68 | 0.61 | 0.76 | 0.65 | 0.75 |
| | M30103 | 0.56 | 0.84 | 0.52 | 0.68 | 0.55 | 0.75 | 0.57 | 0.76 |
| | M33217 | 12.80 | 0.49 | 0.83 | 0.66 | 11.61 | 12.84 | 11.92 | 12.81 |
| | M36296 | 0.55 | 0.59 | 0.85 | 0.72 | 0.42 | 0.76 | 0.42 | 0.82 |
| | M40067 | 0.30 | 0.60 | 0.93 | 0.77 | 0.47 | 0.29 | 0.47 | 0.27 |
| | M42401 | 0.36 | 0.60 | 0.70 | 0.65 | 0.34 | 0.40 | 0.33 | 0.42 |
| α1-AT | M53110 | 0.11 | 0.43 | 0.98 | 0.70 | 0.04 | 0.17 | 0.05 | 0.18 |
| | M53531 | 0.04 | 0.62 | 0.80 | 0.71 | 0.03 | 0.12 | 0.03 | 0.13 |
| | M54605 | 0.18 | 0.76 | 0.61 | 0.68 | 0.20 | 0.16 | 0.16 | 0.18 |
| TF | M78715 | 1.05 | 0.78 | 0.85 | 0.81 | 1.46 | 0.78 | 1.38 | 0.73 |
| | M79909 | 1.28 | 0.63 | 0.87 | 0.75 | 1.71 | 1.13 | 1.69 | 1.05 |
| | M83689 | 0.04 | 0.63 | 0.72 | 0.67 | 0.03 | 0.10 | 0.05 | 0.10 |
| | M84133 | 0.02 | 0.69 | 0.74 | 0.72 | 0.02 | 0.05 | 0.03 | 0.06 |
| | M90834 | 0.18 | 0.52 | 0.80 | 0.66 | 0.22 | 0.18 | 0.21 | 0.17 |
| | M91878 | 0.19 | 0.48 | 0.89 | 0.69 | 0.25 | 0.19 | 0.25 | 0.19 |
| | M92935 | 0.24 | 0.59 | 0.89 | 0.74 | 0.29 | 0.21 | 0.29 | 0.20 |
| | M105778 | 0.06 | 0.65 | 0.80 | 0.73 | 0.09 | 0.05 | 0.09 | 0.04 |
| IgG | M106624 | 0.09 | 0.56 | 0.91 | 0.74 | 0.12 | 0.08 | 0.12 | 0.08 |

Example 4

ApoA-I and ApoA-I Mimetic Peptides Inhibit Tumor Development in a Mouse Model of Ovarian Cancer This example demonstrates that overexpression of human apoA-I in transgenic mice inhibits tumor growth and improves survival in a mouse model of ovarian cancer and treatment with the apoA-I mimetic peptides, L-4F, D-4F, or L-5F decreases tumor burden in mice injected with ID8 cells (a mouse epithelial ovarian cancer cell line). We further demonstrate that apoA-I mimetic peptides bind LPA with remarkable affinity and reduce serum LPA levels in mice. Our results demonstrate, for the first time, that apoA-I plays an important role in the progression of ovarian cancer, and apoA-I and apoA-I mimetic peptides may serve as a novel class of therapeutic agents for the treatment of ovarian cancer.

Materials and Methods

Mice. The Animal Research Committee at UCLA approved all mouse protocols. C57BL/6-Tg (APOA-I) 1Rub/J female mice (hApoA-I/Tg) carrying the human apoA-I transgene and the C57BL/6J female littermates were purchased from The Jackson Laboratory (Bar Harbor, Me.).

ID8 cell line (a mouse ovarian epithelial papillary serous adenocarcinoma cell line) was a generous gift from Dr. K. F. Roby (Center for Reproductive Sciences, University of Kansas Medical Center).

Survival studies. Nine-week-old hApoA-I/Tg mice and C57BL6/J mice were given an i.p. injection containing $8 \times 10^6$ ID8 cells in a total volume of 0.8 ml of DMEM (without supplements). The mice were monitored with weekly weight and abdominal girth measurements until death.

Tumor load studies. For s.c. studies, hApoA-I/Tg mice or C57BL/6J mice (9 weeks old), were given a 0.5 ml s.c.

injection of 5×10⁶ ID8 cells prepared as a single cell suspension in PBS mixed with an equal volume of the cold Matrigel (10 mg/ml of protein). The mice were sacrificed 5 weeks after injection and tumor volumes were measured using the formula $V=1/2(L\times W^2)$. For i.p. studies, hApoA-I/Tg mice or C57BL/6J mice (9 weeks old), were given an i.p. injection containing 8×10⁶ ID8 cells in a total volume of 0.8 ml of DMEM (without supplements). Nine weeks after the injection the mice were sacrificed and tumor loads were assessed by counting the number of tumor nodules on the parietal peritoneal surfaces and the visceral peritoneal surfaces of the intestine, liver, kidney and spleen.

Cell culture experiments. ID8, OV2008 and A2780 cells (2000 cells/well) were first cultured in complete medium in 96-well culture plates, and 24 hours later the medium was replaced with serum and growth factor free medium. Following an overnight incubation, the cells were either left untreated (no treatment) or treated with 100 μg/ml of human apoA-I or apoA-II, or treated with 10 μg/ml of apoA-I mimetic peptides, L-4F or sc-4F or L-5F. Cells were incubated for an additional 48 hours and assayed for viability using the MTS assays kit (Promega, Madison, Wis.) according to manufacturer's protocol. For proliferation assay, cells were labeled with BrdU for the last 4 h of the 48-hour incubation. Cells were subsequently washed, fixed, and incubated with mouse anti-BrdU antibody for 1 h at room temperature and detected by a peroxidase-coupled goat anti-mouse secondary antibody (Calbiochem, San Diego, Calif.). Absorbance was measured using dual wavelengths 450 and 540 nm.

LPA binding affinity and serum LPA levels. LPA (20:4) was purchased from Avanti Polar Lipids (Alabaster, Ala.). Binding affinity of LPA for apoA-I and L-4F was determined as described previously (26). Serum LPA levels were determined as described previously (56).

Statistical analyses. The data are shown as means±S.D. for each group. We performed statistical analyses by unpaired t test. All results were considered statistically significant at $P<0.05$.

Results

Overexpression of human apoA-I improves overall survival in a mouse model of ovarian cancer. We first examined the effect of apoA-I overexpression on overall survival in a mouse (C57BL/6J) model of ovarian cancer (21-23). The survival studies were performed in wild-type C57BL/6J mice and hApoA-I/Tg mice on a C57BL/6J background. The Kaplan Meier survival curves shown in FIG. 1A demonstrate that following an IP injection of ID8 cells, hApoA-I/Tg mice survived longer compared to C57BL/6J mice (hazard ratio 3.2, p<0.0001). None of the C57BL/6J mice survived beyond 87 days. In contrast, all but one of the hApoA-I/Tg mice survived past 87 days. The median time to death was 86 days in the C57BL/6J mice and 106 days in the hApoA-I/Tg mice (FIG. 1a).

Tumor burden following ID8 cell injection is significantly decreased in hApoA-I/Tg mice compared to wild-type C57BL/6J mice. To determine whether improved survival in hApoA-I/Tg mice was due to reduced tumor burden, hApoA-I/Tg and C57BL/6J mice were injected with ID8 cells by subcutaneous (s.c.) injection (5×10⁶ cells per mouse; n=9 for C57BL/6J and n=10 for hApoA-I/Tg) or intraperitoneal (i.p.) injection (8×10⁶ cells per mouse; n=13 per group), and tumor burden was analyzed after 5 weeks and 9 weeks, respectively. The size of flank tumors five weeks after s.c. injection of ID8 cells was significantly larger in C57BL/6J mice compared to hApoA-I/Tg mice (184 mm³ vs. 50 mm³, p<0.01, FIGS. 1b and 1c). Moreover, following i.p. injection of ID8 cells, tumor load was markedly greater in C57BL/6J mice when compared to hApoA-I/Tg mice (average number of tumor nodules on liver, kidney, spleen, diaphragm and intestines, collectively, were 55 in C57BL/6J mice and only 29 in the hApoA-I/Tg mice, p<0.01) (FIGS. 1d and 1e).

Tumor development following ID8 cell injection is significantly decreased in mice injected with apoA-I mimetic peptides, L-5F and L-4F. To determine whether apoA-I mimetic peptides could reduce tumor development similar to human apoA-I, wild-type C57BL/6J mice were first injected with ID8 cells s.c. in the flank or i.p. The mice received L-5F (10 mg/kg) or vehicle ABCT buffer (50 mM ammonium bicarbonate, pH7.0, containing 0.1 mg/ml Tween-20) by s.c. injection at a site distant from the site where the ID8 cells were injected daily for five weeks (for flank tumors) and nine weeks (for i.p. tumors). The size of the flank tumors was significantly larger in C57BL/6J mice treated with ABCT buffer compared to mice treated with L-5F (310 mm³ vs. 52 mm³, p<0.05) (FIG. 2a). Following i.p. injection, the number of tumor nodules was greater in C57BL/6J mice treated with ABCT buffer compared to mice treated with L-5F (average number of tumor nodules on liver, kidney, spleen, diaphragm and intestines, collectively, 82 vs. 44, p<0.05) (FIG. 2b). L-4F treated mice also developed significantly smaller flank tumors when compared to mice injected with a control peptide, scrambled-4F (sc-4F) (108 mm³ vs. 53 mm³, p<0.01) (FIGS. 2c and 2d). Moreover, when L-4F and sc-4F were given two weeks after the injection of ID8 cells, the mice receiving L-4F developed significantly smaller flank tumors when compared to sc-4F treated mice (155 mm³ vs. 80 mm³, p<0.01) (FIG. 2e).

Figure 3:
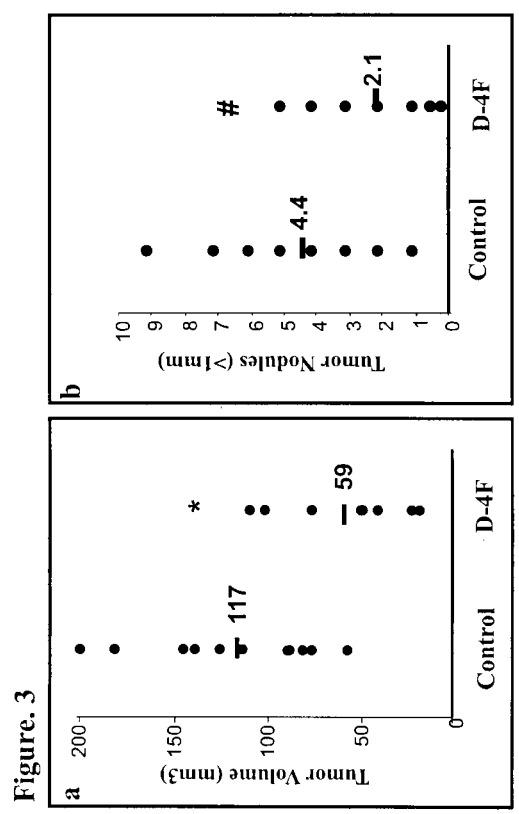
FIG. 3: ID8 cell-mediated tumor size is significantly decreased in C57BL/6J mice treated with apoA-I mimetic peptide, D-4F, in drinking water. Flank tumors and i.p. tumors were established in C57BL/6J (n=11 per group) as described under Materials and Methods. For each experiment two groups of mice were used. One group received regular drinking water ad libitum (Control) and the other group received D-4F (D-4F) in drinking water at a concentration of 300 μg/ml starting on the day of flank or i.p. injections. (a) Mice were sacrificed 5 weeks after flank injection and tumor volumes were calculated. (b) Tumor burden was analyzed at nine weeks following i.p. injections. Average tumor nodules >1 mm on liver, spleen, kidney, diaphragm and intestines, were counted for each mouse and data from each group was combined and analyzed. # Denotes $p<0.05$ and * denotes $p<0.01$.

Tumor development following ID8 injection is significantly decreased in mice given the apoA-I mimetic peptide, D-4F in drinking water. D-4F has the same sequence as L-4F but it is synthesized from all D-amino acids and can be administered orally (24-25). We next examined whether D-4F given in drinking water is effective in reducing tumor development in wild-type C57BL/6J mice. Mice receiving D-4F in drinking water at a concentration of 300 μg/ml starting on the day of flank injection until sacrifice (5 weeks), showed significant reduction in flank tumor size (117 mm³ vs. 59 mm³, p<0.01) compared to C57BL/6J mice receiving regular drinking water (FIG. 3a). Furthermore, mice receiving D-4F in drinking water (300 μg/ml) starting on the day of i.p. injection until sacrifice (9 weeks), showed a significant reduction in the number of tumor nodules (average number of tumor nodules >1 mm, 4.4 vs. 2.1, p<0.05) compared to C57BL/6J mice receiving drinking water without peptide (FIG. 3b).

Effect of apoA-I and apoA-I Mimetic Peptides on ID8 Cell Viability and Proliferation In Vitro.

Figure 4:
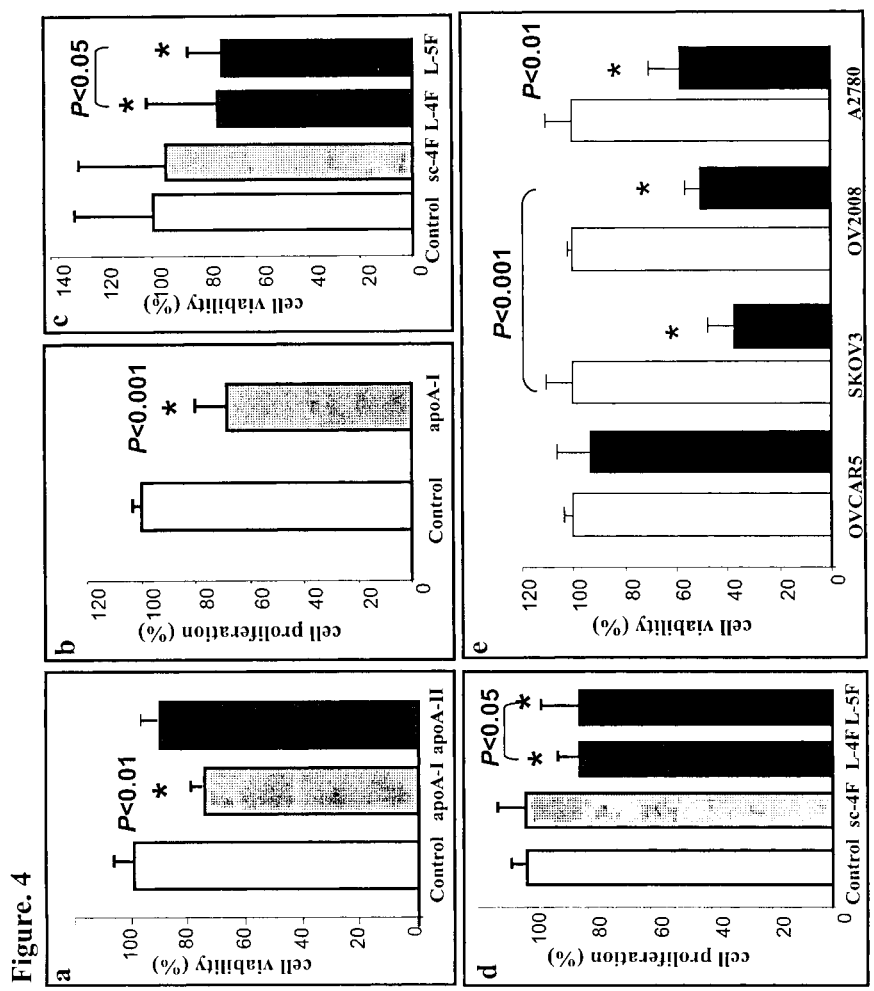
FIG. 4: ApoA-I and apoA-I mimetic peptides reduce viability and inhibit ID8 cell proliferation, and also reduce cell viability of cis-platinum resistant human ovarian cancer cell lines in vitro. ID8 cells were cultured as described under Materials and Methods, and incubated with either apoA-I or apoA-II (100 μg/ml) or apoA-I mimetic peptides (L-5F, L-4F or sc-4F at a concentration of 10 μg/ml) for 48 hours. (a) (c) (e) Cells were assayed for viability using the MTS assay kit. (b) (d) BrdU incorporation was analyzed as described in Example 4. Data are presented as the mean±SD of % of control cells. All experiments were performed in triplicate and each assay was carried out in quadruplicates. (E) OVCAR5, SKOV3, OV2008, and A2780 cell lines were cultured as described in Materials and Methods and were either untreated (open bars) or treated with 10 µg/ml of L-4F (closed bars).

To examine the mechanism(s) by which apoA-I and apoA-I mimetic peptides inhibit ID8 cell mediated tumor development in mice, the effect of apoA-I and apoA-I mimetic peptides on ID8 cell viability was determined in vitro. Cell viability was more than 20% lower (p<0.01) in ID8 cells 48 hours following treatment with human apoA-I (100 μg/ml) when compared to no treatment and compared to cells treated with human apoA-II (100 μg/ml), which is another protein in HDL (FIG. 4a). Moreover, apoA-I significantly inhibited proliferation of ID8 cells (p<0.001) as measured by BrdU incorporation (FIG. 4b). Similarly, apoA-I mimetic peptides, L-5F and L-4F, but not sc-4F (all at 10 μg/ml) inhibited ID8 cell viability (FIG. 4c) and proliferation (FIG. 4d). Furthermore, under identical experimental conditions neither apoA-I nor apoA-I mimetic peptides affected the viability and proliferation of mouse primary ovarian epithelial cells.

ApoA-I mimetic peptides inhibit viability of human ovarian cancer cell lines. To examine whether apoA-I peptides are effective in human ovarian cancer cell lines, we analyzed cell viability following apoA-I mimetic peptide addition in four cis-platinum resistant cell lines. L-4F at 10 μg/ml significantly inhibited cell viability in three out of four human ovarian cancer cell lines that are known to be cis-platinum resistant (FIG. 4e).

Figure 5:
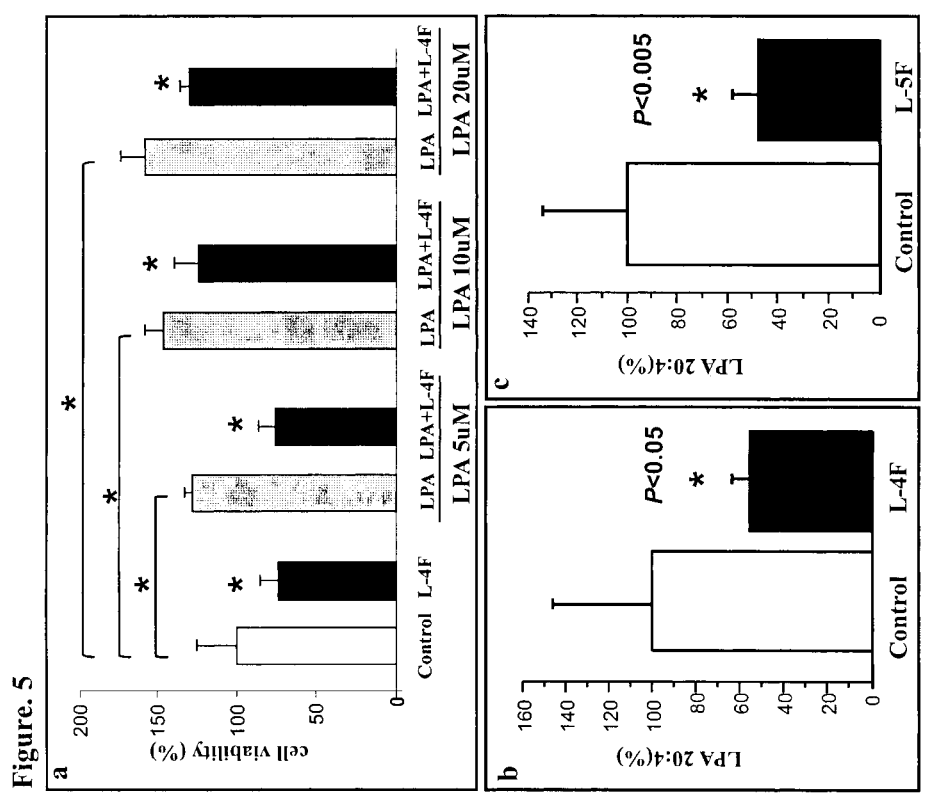
FIG. 5: ApoA-I mimetic peptides inhibit LPA induced proliferation of ID8 cells and reduce serum LPA levels in mice injected with ID8 cells. (a) ID8 cells were cultured as described under Materials and Methods, and incubated with either apoA-I mimetic peptides L-4F (10 µg/ml) or LPA at a concentration 5 µM, 10 µM, 20 µM, or cells treated with both L-4F and LPA for 48 hours. Data are represented as the mean±SD of % of control cells. All experiments were performed in triplicate and each assay was carried out in quadruplicates. * Denotes p<0.05. (b) (c) Serum LPA levels from the mice described in FIGS. 2*b* and 2*c* were determined as described in Example 4. The values shown are the Mean±SD.

ApoA-I mimetic peptides inhibit LPA induced proliferation of ID8 cells and reduce serum LPA levels in mice injected with ID8 cells. LPA has been identified as an important mediator of tumor development, progression, and metastases in humans (18-19). Li et al. recently demonstrated that LPA stimulates cell migration, invasion, and colony formation as well as tumorigenesis/metastasis of mouse ovarian cancer in immunocompetent mice (20). We have previously demonstrated that apoA-I and apoA-I mimetic peptides bind lipids with high affinity and apoA-I mimetic peptides are several to 4-6 orders of magnitude better than apoA-I in binding oxidized lipids (26). We first examined whether apoA-I and L-4F can bind LPA using surface plasmon resonance as described previously (26). Binding affinity is defined by the equation $K_D = k_d/k_a$ where $k_d$=dissociation rate constant and $k_a$=association rate constant. Thus, the larger $K_D$ the weaker binding, and the smaller $K_D$ the stronger binding. Both apoA-I and L-4F bind LPA, although similar to the binding of other oxidized lipids, L-4F binds LPA better than apoA-I by 6 orders of magnitude (Table 1). Moreover, as expected, LPA (5-20 μM) significantly improved ID8 cell growth (FIG. 5a) and L-4F significantly inhibited LPA-induced viability at all doses tested (FIG. 5a). Furthermore, in the mouse experiments shown from FIG. 2 serum LPA levels were significantly reduced in mice receiving L-4F (FIG. 5b) and L-5F (FIG. 5c), when compared to their corresponding control mice.

Discussion

Inflammation and oxidative stress contribute to the etiology of almost every known disease. Reactive oxygen species generated by enzymatic and non-enzymatic systems modify lipids and sterols, producing oxidized lipids and oxidized sterols, which if unchecked produce undesirable inflammation and more oxidative stress. Under normal physiological conditions, anti-oxidant enzyme systems and HDL-associated proteins and enzymes reduce oxidative stress. However, under a variety of inflammatory conditions these anti-oxidant defense mechanisms are often reduced probably as an evolutionary mechanism to promote oxidative stress to kill invading microbes.

Oxidative stress has long been associated with the pathophysiology of cancer. Highly metastatic and invasive tumors appear to flourish under conditions of maximum oxidative stress (27).

Reactive oxygen species may be conducive to the vitality of cancer cells and drive signaling transduction pathways that leads to activation of redox-sensitive transcription factors and genes involved in cancer cell growth, proliferation, and survival (28-29). Since oxidized lipid mediated inflammation appears to be common (30-31), it is not surprising that lipoproteins may be a central modulator/regulator of diseases including cancer and atherosclerosis in which inflammation is an important component.

Indeed, in a large cohort of early stage breast cancer survivors, statin therapy was associated with improved prognosis, and decreased risk of recurrence (32). The Health Professionals Follow-up Study identified statin users to have a significantly lower risk of metastatic and fatal disease in prostate cancer patients (33). In women with advanced stage epithelial ovarian cancers, a statistically significant longer time to progression and improved overall survival was observed for those patients also on statin therapy (34) and more recently, LDL was demonstrated to be a significant predictor of clinical outcome in advanced epithelial ovarian cancer patients (35). In another study, paraoxonase (PON1) activity (a key anti-oxidant protein associated with HDL) correlated inversely with stage, grade and CA-125 level of ovarian cancer (36). Decreased PON1 activity and increased lipid hydroperoxide levels are suggested to play a role in the initiation and progression of epithelial ovarian cancer (36). All of these studies allude to the importance of circulating lipoproteins and their metabolism in the regulation of tumorigenesis.

ApoA-I is the major protein constituent of HDL. Decreased apoA-I levels have been reported in the serum of patients with pancreatic cancer, gastric cancer, and ovarian cancer (4,37-38). Serum apoA-I levels are also down regulated in patients with lymphoblastic leukemia (39). Scribano et al. (40) showed that patients with acute lymphoblastic leukemia who achieved remission after receiving chemotherapy showed significant increases in apoA-I levels. In this report, we demonstrate that apoA-I plays an important role in ovarian tumorigenesis. We are the first to demonstrate that overexpression of human apoA-I is associated with an improved overall survival in a mouse model of ovarian cancer (FIG. 1). The improved survival in hApoA-I/Tg mice was associated with a significant decrease in overall tumor burden (FIG. 2) following injection of a murine derived ovarian adenocarcinoma cell line (ID8), which is histologically similar to human ovarian adenocarcinoma.

Over the last eight years, peptide mimetics of apoA-I have been tested in animal models for their ability to confer the anti-inflammatory and anti-oxidant properties associated with apoA-I. ApoA-I mimetic peptides markedly reduce atherosclerosis in animal models (11,41). Furthermore, several published studies of apolipoprotein mimetic peptides in models of inflammatory disorders other than atherosclerosis suggest that they have efficacy in a wide range of inflammatory conditions (10,13), including, in animal models of dyslipidemia (10-11, 42-43), diabetes and vascular inflammation (44-48) renal disease (12,49), sepsis (50), and Alzheimer's disease (51). Our studies demonstrate that apoA-I mimetic peptides are very effective in preventing the development of tumors (FIG. 2 and FIG. 3) in immunocompetent mice injected with ID8 cells.

Figure 2:
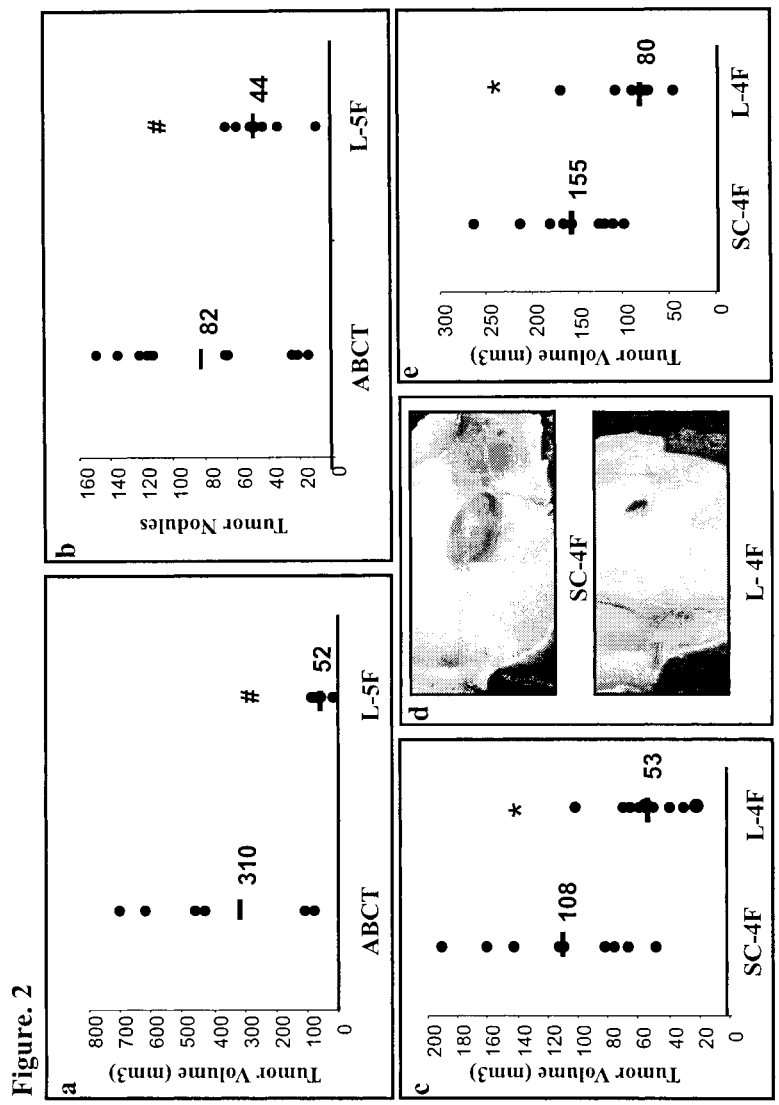
FIG. 2: ID8 cell-mediated tumor sizes are significantly decreased in C57BL/6J mice injected with apoA-I mimetic peptides. Flank tumors and i.p. tumors were established in C57BL/6J female mice (n=10 per group) as described in Example 4. (a) Mice were sacrificed 5 weeks after ID8 cell s.c. injection and tumor volumes were calculated. The data shown are for mice receiving vehicle alone (ABCT) or vehicle containing L-5F starting on the day of injection of the ID8 cells. (b) Mice were sacrificed 9 weeks after i.p. injection of ID8 cells and the average number of tumor nodules on liver, spleen, kidney, diaphragm and intestines, were counted for each mouse and data from each group were combined and analyzed. The data shown are for mice receiving vehicle alone (ABCT) or vehicle containing L-5F starting on the day of injection of the ID8 cells. (c) Mice were sacrificed 5 weeks after flank injection of ID8 cells and tumor volumes were calculated. The data shown are for mice receiving scrambled 4F (sc-4F) or L-4F starting on the day of injection of the ID8 cells. Both sc-4F and L-4F were administered s.c. at a site distant from the site where the ID8 cells were injected. (d) Representative tumors are shown from mice in panel "c". (e) Experimental details are identical to (c) except that the injections of L-4F and sc-4F were started two weeks after the injection of ID8 cells in the flank. # Denotes $p<0.05$ and * denotes $p<0.01$.

It has been recently demonstrated that apoA-I mimetic peptides exert their anti-inflammatory properties, in large part, by their ability to bind pro-inflammatory lipids. LPA, a pro-inflammatory lysophospholipid, is implicated in the etiology of a number of human cancers including ovarian cancer (14). LPA has been reported to enhance tumor growth of ID8 cells and ascites formation in female C57BL/6 mice (20). We demonstrated that apoA-I and apoA-I mimetic peptides bind LPA but the apoA-I mimetic peptides bind LPA with an affinity that is six orders of magnitude greater than apoA-I. In vitro, LPA-induced cell growth is prevented by L-4F (FIG. 5a) suggesting that the apoA-I mimetic peptides are able to inhibit LPA action on ID8 cells. Importantly in vivo, LPA levels were significantly reduced in mice that received apoA-I mimetic peptides when compared to control mice (FIG. 5), and the relative serum LPA levels correlated with the tumor burden in these two groups of mice (FIG. 2). Taken together, our results suggest that a plausible mechanism of action for apoA-I mimetic peptides in this model is to bind and aid in reducing the levels of pro-tumorigenic lipids such as LPA.

Our current findings suggest that inhibition of cell growth is the dominant mechanism. We did not see differences in apoptosis but did see significant differences in BrdU incorporation in cells following peptide treatment. In vitro the apoA-1 mimetic peptide, L-4F, inhibited the viability of human papillary serous adenocarcinoma cell lines resistant to cis-platinum namely, SKOV3, OV2008, and A2780 (FIG. 4e). Some human ovarian cancer cell lines appear to have high levels of the dual specificity MAP kinase phosphatase, MKP-1 which is necessary for their resistance to cis-platinum (52). We previously reported that MKP-1 is markedly induced by oxidized phospholipids (53-54) of the kind bound by L-4F with very high affinity. It will be interesting in future studies to determine if L-4F treatment decreased MKP-1 in these cis-platinum resistant cell lines. These data have potentially important clinical implications since the vast majority of patients treated for advanced stage ovarian cancer will succumb to their disease secondary to the development of cis-platinum resistant recurrent disease (55).

The data suggest that apoA-I is not only a biomarker for the detection of early stage ovarian cancer, but apoA-I and apoA-I mimetic peptides are also be promising therapeutic agents for the treatment of ovarian cancer.

REFERENCE CITED IN EXAMPLE 4

1. Edwards B K, et al. (2010) *Cancer* 116:544-73.
2. Nossov V, et al. (2008) *Am J Obstet Gynecol* 199:215-23.
3. Kozak K R, et al. (2003) *Proc Natl Acad Sci USA* 100:12343-8.
4. Kozak K R, et al. (2005) *Proteomics* 5:4589-96.
5. Su F, et al. (2007) *Biomark Insights* 2:369-75.
6. Nosov V, et al. (2009) *Am J Obstet Gynecol* 200: 639.e1-5.
7. Tardif J C, Heinonen T, Nobl S (2009) *Curr Atheroscler Rep* 11:58-63.
8. Navab M, et al. (2005) *Circ Res* 97:524-32.
9. Reddy S T, et al. (2006) *Expert Opin Investig Drugs* 15:13-21.
10. Van Lenten B J, et al. (2008) *Curr Opin Investig Drugs* 9:1157-62.
11. Navab M, et al. (2009) *J Lipid Re* 50:1538-47.
12. Vaziri N D, et al. (2009) *Kidney Int* 76:437-44.
13. Van Lenten B J, et al. (2009), *Curr Atheroscler Rep* 11:52-7.
14. Xu Y, et al. (1995) *Biochem J* 309:933-40.
15. Xiao Y J, et al. (2001) *Anal Biochem* 290:302-13.
16. Boucharaba A, et al. (2006) *Proc Natl Acad Sci USA* 103:9643-8.
17. Kitayama J, et al. (2004) *Breast Cancer Res* 6:R640-6.
18. Baker D L, et al. (2002) *JAMA* 287:3081-2.
19. Sutphen R, et al. (2004) *Cancer Epidemiol Biomarkers Prev* 13:1185-91.
20. Li H, et al. (2009) *Mol Cancer Ther* 8:1692-701.
21. Roby K F, et al. (2000) *Carcinogenesis* 21:585-91.
22. Greenaway J, et al. (2009) *Mol Cancer Ther* 8:64-74.
23. Pengetnze Y, et al. (2003) *Biochem Biophys Res Commun* 309:377-83.
24. Navab M, et al. (2002) *Circulation* 105:290-2.
25. Navab M, et al. (2004) *Circulation* 109:3215-20.
26. Van Lenten B J, et al. (2008) *J Lipid Res* 49:2302-11.
27. Nicotera T M, et al. (1994) *Cancer Res* 54:3884-8.
28. Loo G (2003) *J Nutr Biochem* 14:64-73.
29. Hu Y, et al. (2005) *J Biol Chem* 280:39485-92.
30. Bochkov V N, et al. (2010) *Antioxidants & Redox Signaling* 12:1009-1059.
31. Wang L, et al. (2009) *J Lipid Res* 50:204-213.
32. Kwan M L, et al. (2008) *Breast Cancer Res Treat* 109:573-9.
33. Platz E A, et al. (2006) *J Natl Cancer Inst* 98:1819-25.
34. Elmore R G, et al. (2008) *Gynecol Oncol* 111:102-5.
35. Li A W, et al. (2009) *Gynecol Oncol* 116:78-81.
36. Camuzcuoglu H, et al. (2009) *Gynecologic Oncology* 112:481-485.
37. Ehmann A, et al. (2007) *Pancreas* 34:205-14.
38. Takaishi S, Wang T C (2007) *Cancer Sci* 98:284-293.
39. Halton J M, et al. (1998) *Cancer* 83:379-84.
40. Scribano D, et al. (1996) *Haematologica* 81:343-45.
41. Navab M, et al. (2010) *Arterioscler Thromb Vasc Biol* 30:164-8.
42. Van Lenten B J, et al. (2007) *J Lipid Res* 48:2344-53.
43. Mandavi H, et al. (2009) *Curr Opin Lipidol* 20:157-8.
44. Van Lenten B J, et al. (2002) *Circulation* 106:1127-32.
45. Watanabe J, et al. (2009) *J Biol Chem* 284:18292-301.
46. Ou J, et al. (2005) *Circ Res* 97:1190-97.
47. Peterson S J, et al. (2008) *J Lipid Res* 49:1658-69.
48. Peterson S J, et al. (2009) *J Lipid Res* 50:1293-304.
49. Kaysen G A (2009) *Kidney Int* 76:359-61.
50. Zhang Z, et al. (2009) *Am J Physiol Heart Circ Physiol* 297:H866-73.
51. Handattu S P, et al. (2009) *Neurobiol Dir* 34:525-34.
52. Wang J, et al. (2009) *Cell Cycle* 8:3191-3198.
53. Reddy S T, et al. (2002) *Vasc Pharmacol* 38:211-218.
54. Reddy S T, et al. (2004) *Arterioscler Thromb V asc Biol* 24:1676-1681.
55. Cannistra S A (2004) *N Engl J Med* 351:2519-2529.
56. Murph M, et al. (2007) *Methods Engmol* 433:1-25.

Example 5

D-4F, an apoA-I Mimetic Peptide, Inhibits Proliferation and Tumorigenicity of Epithelial Ovarian Cancer Cells by Upregulating the Antioxidant Enzyme MnSOD To delineate the mechanism(s) of action of apoA-I mimetic peptides in tumor development, the effect of D-4F on the antioxidant status and on the gene expression and function of antioxidant enzymes in ID8 cells and in a mouse model was examined. D-4F treatment significantly reduces the viability and proliferation of ID8 cells, with a concomitant improvement of the antioxidant status of ID8 cells as measured by lipid peroxidation, protein carbonyl, superoxide anion, and hydrogen peroxide levels. D-4F treatment induces MnSOD (but not CuZnSOD) mRNA, protein, and activity. Inhibition of MnSOD in ID8 cells using shRNA vectors abrogates the inhibitory effects of D-4F on ID8 cell viability and proliferation. Moreover, tumor development from ID8 cells carrying shRNA for MnSOD were unaffected by D-4F treatment. These results suggest that the inhibitory effects of D-4F on ID8 cell proliferation and tumor development are mediated, at least in part, by the induced expression and activity of MnSOD. (See details at Ganapathy et al., Int J Cancer. 2011 Mar. 21. doi: 10.1002/ijc.26079.)

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of inhibiting the proliferation of gynecologic cancer cells in vivo, comprising contacting the cancer cells in vivo with apolipoprotein A-1 (ApoA-1).

2. The method of claim 1, wherein the ApoA-1 has the amino acid sequence of native ApoA-1 shown in SEQ ID NO: 1.

3. The method of claim 1, wherein the ApoA-1 is ApoA-1 Milano and has the amino acid sequence shown in SEQ ID NO: 2.

4. A method of inhibiting tumor growth in a subject having gynecologic neoplasia, the method comprising administering to the subject an effective amount of ApoA-1 and, optionally, a pharmaceutical excipient.

5. A method of treating gynecologic cancer in a subject, the method comprising administering to the subject an effective amount of ApoA-1 and, optionally, a pharmaceutical excipient.

6. The method of claim 1, wherein the cancer is ovarian, endometrial, cervical, vaginal or vulvar cancer.

7. The method of claim 4, wherein the ApoA-1 is administered as high-density lipoprotein (HDL).

8. The method of claim 4, wherein the ApoA-1 is administered as recombinant ApoA-1.

9. The method of claim 4, wherein the ApoA-1 is administered transdermally, intravenously, intraperitoneally, subcutaneously, or intradermally.

10. The method of claim 4, wherein the subject is mammalian.

11. The method of claim 4, wherein the subject is human.

12. The method of claim 5, wherein the cancer is ovarian cancer.

13. The method of claim 4, wherein the effective amount is an amount sufficient to significantly decrease tumor size.

14. The method of claim 5, wherein the effective amount is an amount sufficient to significantly decrease tumor size.

* * * * *

SEQUENCE LISTING

<160> NUMBER OF SEQ ID NOS: 3

<210> SEQ ID NO 1
<211> LENGTH: 243
<212> TYPE: PRT
<213> ORGANISM: Homo sapiens

<400> SEQUENCE: 1

Asp Glu Pro Pro Gln Ser Pro Trp Asp Arg Val Lys Asp Leu Ala Thr
1               5                   10                  15

Val Tyr Val Asp Val Leu Lys Asp Ser Gly Arg Asp Tyr Val Ser Gln
            20                  25                  30

Phe Glu Gly Ser Ala Leu Gly Lys Gln Leu Asn Leu Lys Leu Leu Asp
        35                  40                  45

Asn Trp Asp Ser Val Thr Ser Thr Phe Ser Lys Leu Arg Glu Gln Leu
50                  55                  60

Gly Pro Val Thr Gln Glu Phe Trp Asp Asn Leu Glu Lys Glu Thr Glu
65                  70                  75                  80

Gly Leu Arg Gln Glu Met Ser Lys Asp Leu Glu Glu Val Lys Ala Lys
                85                  90                  95

Val Gln Pro Tyr Leu Asp Asp Phe Gln Lys Lys Trp Gln Glu Glu Met
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Arg Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Arg Gln Gly Leu Leu Pro Val Leu Glu Ser
210                 215                 220

Phe Lys Val Ser Phe Leu Ser Ala Leu Glu Glu Tyr Thr Lys Lys Leu
225                 230                 235                 240

Asn Thr Gln

<210> SEQ ID NO 2
<211> LENGTH: 243
<212> TYPE: PRT
<213> ORGANISM: Homo sapiens

<400> SEQUENCE: 2

Asp Glu Pro Pro Gln Ser Pro Trp Asp Arg Val Lys Asp Leu Ala Thr
1               5                   10                  15

Val Tyr Val Asp Val Leu Lys Asp Ser Gly Arg Asp Tyr Val Ser Gln
            20                  25                  30

Phe Glu Gly Ser Ala Leu Gly Lys Gln Leu Asn Leu Lys Leu Leu Asp
        35                  40                  45

Asn Trp Asp Ser Val Thr Ser Thr Phe Ser Lys Leu Arg Glu Gln Leu
50                  55                  60

Gly Pro Val Thr Gln Glu Phe Trp Asp Asn Leu Glu Lys Glu Thr Glu
65                  70                  75                  80

```
Gly Leu Arg Gln Glu Met Ser Lys Asp Leu Glu Val Lys Ala Lys
                85                  90                  95

Val Gln Pro Tyr Leu Asp Asp Phe Gln Lys Lys Trp Gln Glu Met
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
    130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Cys Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Arg Gln Gly Leu Leu Pro Val Leu Glu Ser
    210                 215                 220

Phe Lys Val Ser Phe Leu Ser Ala Leu Glu Glu Tyr Thr Lys Lys Leu
225                 230                 235                 240

Asn Thr Gln

<210> SEQ ID NO 3
<211> LENGTH: 267
<212> TYPE: PRT
<213> ORGANISM: Homo sapiens

<400> SEQUENCE: 3

Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45

Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Glu Met Glu Leu Tyr Arg Gln Lys Val Glu
    130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205
```

```
Gly Gly Ala Arg Leu Ala Glu Tyr His Ala Lys Ala Thr Glu His Leu
    210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
            245                 250                 255

Leu Glu Glu Tyr Thr Lys Lys Leu Asn Thr Gln
            260                 265
```